(12) United States Patent
Hirt et al.

(10) Patent No.: US 6,511,485 B2
(45) Date of Patent: Jan. 28, 2003

(54) DEVICE FOR REMOVAL OF CALCULI

(75) Inventors: Joachim Hirt, Constance (DE);
Wolfgang Merkle, Meersburg (DE)

(73) Assignee: Ferton Holding S.A. (CH)

( * ) Notice: Subject to any disclaimer, the term of this patent is extended or adjusted under 35 U.S.C. 154(b) by 0 days.

(21) Appl. No.: 09/877,904

(22) Filed: Jun. 8, 2001

(65) Prior Publication Data

US 2002/0010486 A1 Jan. 24, 2002

(30) Foreign Application Priority Data

Jun. 15, 2000 (DE) .......................... 100 29 580

(51) Int. Cl.$^7$ ............................................. A61B 17/22
(52) U.S. Cl. ........................ 606/128; 606/127; 604/22
(58) Field of Search ................. 606/128, 127, 606/170, 169, 2.5; 604/22

(56) References Cited

U.S. PATENT DOCUMENTS

| | | | | |
|---|---|---|---|---|
| 4,178,935 A | | 12/1979 | Gekhman et al. ............ 128/328 |
| 5,116,343 A | * | 5/1992 | Ams et al. ................... 451/165 |
| 5,160,336 A | * | 11/1992 | Favre .......................... 601/108 |
| 5,741,272 A | * | 4/1998 | Kuhne ......................... 604/22 |
| 5,868,756 A | * | 2/1999 | Henry et al. ................. 606/128 |
| 5,911,699 A | | 6/1999 | Anis et al. ................... 606/107 |
| 6,077,285 A | * | 6/2000 | Boukhny ..................... 604/22 |
| 6,214,017 B1 | * | 4/2001 | Stoddard et al. ............ 606/128 |
| 6,391,042 B1 | * | 5/2002 | Cimino ........................ 604/22 |

FOREIGN PATENT DOCUMENTS

| | | |
|---|---|---|
| DE | 20 32 501 A | 1/1972 |
| DE | 19609019 A1 | 9/1997 |
| EP | 03 17 507 A1 | 5/1989 |
| EP | 212 85 B1 | 11/1994 |
| EP | 0421258 B1 | 11/1994 |

OTHER PUBLICATIONS

European Search Report dated Sep. 27, 2001.
EMS Medical GmbH and EMS SA, "Swiss Lithoclast® Master," Edition May 2002.

* cited by examiner

Primary Examiner—Pedro Philogene
(74) Attorney, Agent, or Firm—Ostrolenk, Faber, Gerb & Soffen, LLP

(57) ABSTRACT

Device for removal of calculi by using an intracorporeal lithotripter comprises a metallic probe or sonotrode which is excited by an electrically controlled ultrasonic transducer for generating longitudinal oscillations for the fragmentation of calculi via the distal end of the sonotrode, the sonotrode accommodating a coaxially arranged impact probe which for an alternative fragmentation of calculi transfers shock or pressure forces that are generated by the impact energy of a reversibly driven impact member or projectile which periodically hits against a mass body on the proximal end of the impact probe when its drive is alternatively switched-on.

15 Claims, 2 Drawing Sheets

DEVICE FOR REMOVAL OF CALCULI

FIELD OF THE INVENTION

This invention relates to a device for removal of calculi by using an intracorporeal lithotripter in accordance with the introductory clause of claim 1.

BACKGROUND OF THE INVENTION

When removing calculi from body hollows it becomes necessary in general to crash first in situ those calculi which although still suitable for allowing a natural exit or drainage exceed a predetermined size. It therefore will be necessary to crash or fragment any overdimensioned calculi and to generate particles of a more or less minute size to thereby allow such minimised particles to being spontaneously removed from the body hollow. The minimisation is carried out by acting on the calculi with compressive and tensional forces which in the field of intracorporeal lithotripsy are exercised with the distal end of a metallic probe serving as a wave guide. Such forces result in a blasting-off of fragments from the surface of a calculus for effecting its crashing. However, when fragmenting calculi in this way there exists in general the problem of providing suitable energy transport or energy transfer specifically to those calculi which are to be minimised by avoiding at the same time any disturbing and rather dangerous side effects on the human tissue which therefore should not serve as a backing during such a fragmentation of calculi.

The European Patent EP 0 421 285 B1 discloses a device for removal of calculi by using an intracorporeal lithotripter. The device comprises a metallic probe or sonotrode which by means of an electrically controlled ultrasonic transducer generates longitudinal oscillations. When inserted into the operating passage of an endoscope as used for a fragmentation of calculi the distal end of the metallic probe or sonotrode when in contact with the calculi will crash the same by the transfer of those longitudinal oscillations. The ultrasonic transducer is composed of piezoceramic discs which are arranged within a surrounding casing between a reflector and a horn that are fastened to each other. For periodically oscillating the sonotrode the piezoceramic discs are controlled by a circuit arrangement which comprises a voltage-controlled oscillator the output signal of which is supplied to the piezoceramic discs via an output amplifier and an output transmitter. The circuit arrangement comprises a phase comparator for comparing the phases of the output voltage and of the output current of the output transmitter for generating a control voltage of the oscillator. With a device of this kind it will be possible to crash calculi into very fine fragments with a particle size which in general will not create any problems in sucking-off the calculi fragments through an axial hollow of the sonotrode and extending at its proximal end to an interconnected suction duct which is passed through the ultrasonic transducer. Any minimisation of calculi by means of an intracorporeal lithotripter operating with an ultrasonic transducer must be considered, however, as relatively time-consuming since for a careful handling of the lithotripter at the distal end of the tubular sonotrode it will only be allowable to use ultrasonic frequencies of about 20 to 25 kHz with amplitudes of about 50 $\mu$m for avoiding any damages of the human tissue. There will also be exist certain complications with calculi of a harder consistency which will not allow any spontaneous peeling with such frequencies and amplitudes at the tip of the sonotrode. The operational treatment will accordingly either last very long or will even be impossible.

The European Patent EP 0 317 507 B1 discloses a lithotripter comprising a metallic probe the proximal end of which is arranged for being hit periodically by a pneumatically driven impact member or projectile resulting in an impact energy which is transported along the metallic probe as far as to its distal end so that any calculus when contacted with the tip of the probe will be fragmented under the action of shock or pressure waves. Such shock or pressure wave lithotripters which with alternative designs may also be provided with an electric drive for the impact member or projectile are constructed in general as relatively simple units having nevertheless very high efficiencies with the fragmentation of calculi although it has to be conceded that the handling of such shock or pressure wave lithotripters is still somewhat time-consuming in the context of providing particles that may be spontaneously sucked-off.

SUMMARY OF THE INVENTION

An object of the present invention is to provide a device for removal of calculi by using an intracorporeal lithotripter which will allow a more flexible fragmentation of calculi under consideration of the advantages and the disadvantages of the presently known methods when using lithotripters of the kind as above described.

In accordance with the present invention a device for removal of calculi by using an intracorporeal lithotripter of the kind as referred above is provided which is characterised by the features of the claims.

The present invention offers the possibility that by a combination of a metallic probe or sonotrode that is activated by an electrically controlled ultrasonic transducer on the one side and of an impact probe on the other side which is periodically hit by an impact member or projectile as both united in only a single device an alternative fragmentation of calculi may be exercised by simply switching-on either the electrical control of the ultrasonic transducer or the reversible drive for the projectile. Such an alternative possibility for the handling of the inventive device will certainly result in an optimum fragmentation of any kind of calculi whereby the change-over from either using the one or the other operational mode of the device will not necessitate any exchange of the one probe against the other probe and will also not necessitate any more time-consuming adaption of measures. Such change-over may instead take place instantaneously in any moment of a proceeding fragmentation of calculi. Since the composition of the calculi which are to be fragmented as well as the hardness and the actual size of the calculi is in most cases unknown before, this will therefore allow the surgeon to decide in situ which one of the two operational modes should be used for obtaining an optimum result of the fragmentation.

Other objects, features and advantages of the present invention will become apparent from reading the following description of a preferred embodiment of a device according to the present invention.

BRIEF DESCRIPTION OF THE DRAWINGS

The invention will now be described, by way of example, with reference to the accompanying drawings, in which.

DETAILED DESCRIPTION OF THE PREFERRED EMBODIMENT

Figure 1:
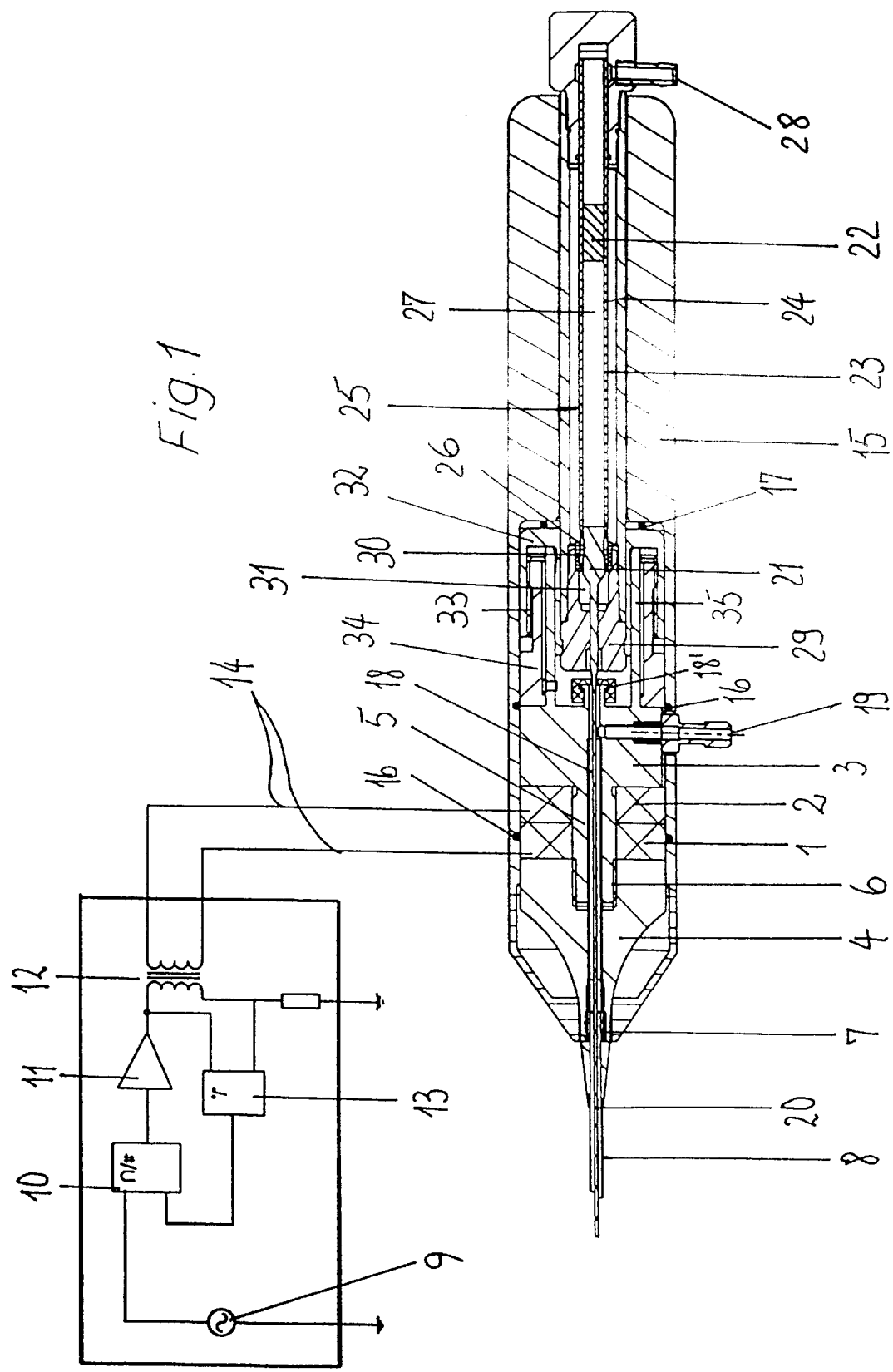
FIG. 1 is a sectional view of the device together with a diagram showing the circuitry of its ultrasonic transducer and FIG. 2 a sectional view on an enlarged scale of a detail of the device in the vicinity of the head portion of the impact probe.

The device for removal of calculi as shown in the drawings comprises an electrically controlled ultrasonic transducer which is designed as a piezoelectric transducer having two piezoceramic discs 1, and 2 as arranged between a reflector 3 and a horn 4. The two piezoceramic discs 1, 2 are centered by an axial protrusion 5 of the reflector 3 which has a screw portion 6 at its end for allowing a screw connection with the horn 4 having at this terminal end of the protrusion 5 a complementary inner thread so that with this arrangement all of the individual parts of the ultrasonic transducer may be fixedly held together. The horn 4 is provided with an enveloping surface in the form of an exponential curve which tapers in the axial direction substantially to the cross-section of a screw portion 7 of a hollow metallic probe or sonotrode 8. The exponential form of the enveloping surface of the horn 4 may be replaced by a conical or by a stepped design of the horn. For obtaining optimum results for the fragmentation of calculi it should be preferred to use a material for both the horn 4 and the metallic probe or sonotrode 8 of substantially the same acoustic impedance whereby as preferred materials high-grade steel or titanium should be used.

For electrically controlling the ultrasonic transducer there is provided a circuit arrangement as generally known per se and comprising a voltage-controlled oscillator 9 the output signal of which is supplied via a voltage-frequency transducer 10 and an interconnected output amplifier 11 to an impedance transformer 12. A phase comparator 13 which is also connected to the transducer 10 is as well interconnected with the impedance transformer 12. The phase comparator 13 is arranged for comparing the phases of the output voltage and the output current to thereby generate a control voltage for the oscillator 9. The impedance transformer 12 is connected via lines 14 to the piezoceramic discs 1, 2 of the ultrasonic transducer so that with this interconnection the metallic probe or sonotrode 8 may be excited for forming periodical longitudinal oscillations.

The arrangement of the ultrasonic transducer comprising the two piezoceramic discs 1, 2, the reflector 3 and the horn 4 is supported on a surrounding casing 15 by elastic support means 16 and 17. A backward portion of the casing 15 is designed more massive then a forward portion of the casing which accommodates the individual elements of the ultrasonic transducer. These individual elements of the ultrasonic transducer, i.e. the two piezoceramic discs 1, 2, the reflector 3 and the horn 4 which are held together by the screw connection of the axial protrusion 5 of the reflector 3, are provided in common with an axial through-bore 18 which is axially aligned with the hollow of the metallic probe or sonotrode 8. The bore 18 is connected with a suction duct 19 which is provided for sucking-off all of the particles which during a fragmentation of calculi by means of the sonotrode 8 are generated in the body hollow. The bore 18 is further dimensioned such that it also accommodates an impact probe 20 which is passed through the hollow of the sonotrode 8 and slightly projects with its tip forwardly of the distal end of the sonotrode when a fragmentation of calculi will be exercised by means of this impact probe 20. The impact probe 20 has a flexible or a rigid design and is passed through a sealing cap 18' which is provided for sealing the axial through-bore 18 on the backside of the reflector 3 of the ultrasonic transducer.

The impact probe 20 forms a working element of a second functional part of the device which instead of the electrically controlled ultrasonic transducer may be used for a fragmentation of calculi. This second functional part may be designed substantially in the same manner as the intracorporeal shock wave lithotripter according to the European Patent EP 0 317 507 B1. The impact probe 20 is therefore provided on its proximal end with a mass body 21 against which an impact force is applied by an impact member or projectile 22 which is driven in a reciprocating manner so that as a result of the impact energy which is transmitted to the mass body 21 shock or pressure waves will be generated in the impact probe 20 which are transferred as pressure pulses via the distal end of the probe to a calculus for its fragmentation by a contact with the tip of the probe. The reversible drive of the impact member or projectile or projectile 22 is preferably of a pneumatic design so that for a description of details of such a pneumatic drive a supplemental reference may be made to the before mentioned EP 0 317 507 B1. The impact member 22 may instead also be driven hydraulically or electromagnetically whereby instead of a direct application of the impact force via the mass body 21 the same may also be applied indirectly.

The impact member or projectile 22 is accommodated in a guide bush 23 which is axially aligned with the through-bore 18 of the ultrasonic transducer and with the hollow of the metallic probe or sonotrode 8. The guide bush 23 accommodates the proximal end of the impact probe 20 which axially projects backwardly with respect to the reflector 3 of the ultrasonic transducer and which is provided with the mass body 21. The guide bush 23 is surrounded by a coaxially arranged outer tube 24 with an annular space inbetween to thereby form a reversing chamber 25 of the pneumatic drive for the impact member or projectile 22. The reversing chamber 25 communicates via a window 26 with a pressure chamber 27 which is formed by the guide bush 23. The pressure chamber 27 is closed by an inlet duct 28 for compressed air which duct has a screw connection with the tube 24.

Figure 2:
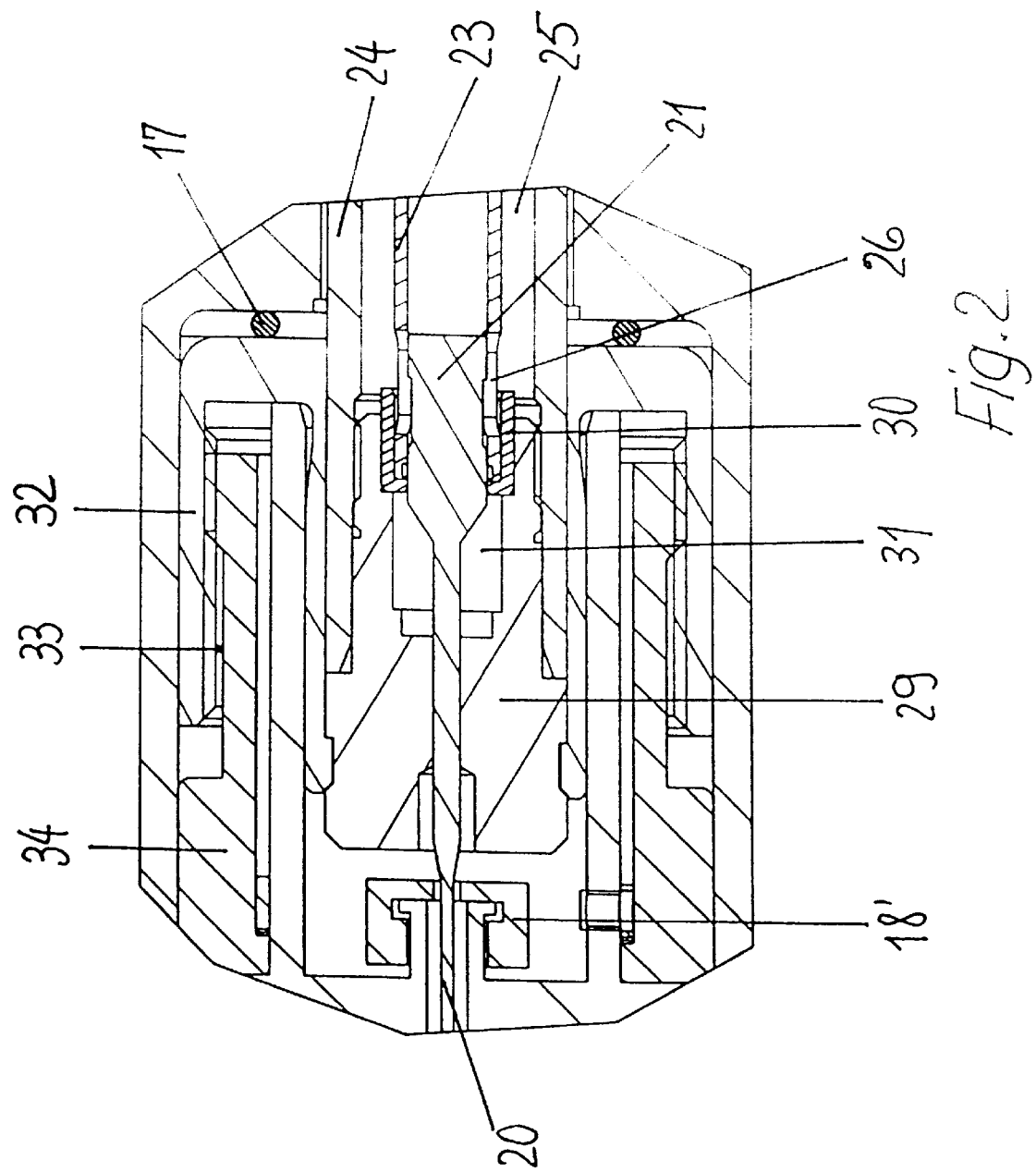

As shown by the details of FIG. 2 there is further provided an axially bored insert body 29 which is inserted into the tube 24 in the vicinity of the proximal end of the impact probe 20. The insert body 29 is sealed against the guide bush 23 by a seal 30 in the vicinity of the window 26. The mass body 21 of the proximal end of the impact probe 20 is supported on this insert body 29 by a damping element 31 which is arranged for damping the impact forces acting on the mass body 21 when the impact member or projectile 22 hits the mass body 21 so that thereby the impact forces will as well be homogenised.

The insert body 29 is held by a screw cap 32 which is screw-connected with a screw portion 23 of a centering bush 34. The centering bush 34 centers the guide bush 23 in co-operation with the insert body 29 and the screw cap 32 inside of a tubular backward protrusion 35 of the reflector 3 whereby this centering is supported on the casing 15 by the elastic supporting means 16 and 17.

Instead of the design of the mass body 21 as an enlarged head portion of the impact probe 20 the mass body may also be provided as a separate member as described in U.S. Pat. No. 5,868,756. With such an alternate arrangement further advantages may be incorporated in that such a separate mass body will act both as a sealing member and as a transfer member for the impact forces of the impact member or projectile as described in this patent.

The electrical control of the ultrasonic transducer could on the other side as well be optimised by providing a switching possibility between a periodic oscillation drive and a pulse wave oscillation drive of the sonotrode which for example may be realised by means of an additional circuit arrangement comprising a voltage source and a capacitor with which a ultrasonic transducer then could alternatively be connected. Reference should be made to the co-pending applications filed on even date herewith, the disclosures of which are incorporated by reference herein.

All of the structural components forming the shock wave lithotripter could be provided as a common subassembly which may be taken out from the surrounding casing so that only the structural components of the ultrasonic transducer will then remain in situ. With such a design the device could then be used in the same manner as a generally known ultrasonic lithotripter independent of its possibility of being on the other side also adapted to be used as a generally known shock wave lithotripter when combined with such a common subassembly forming the structural components of the impact probe.

We claim:

1. A device for removal of calculi by using an intracorporeal lithotripter, comprising:
    a metallic probe or sonotrode serving as a wave guide and being inserted into the operating passage of an endoscope for a fragmentation of calculi via its distal end;
    an electrically controlled ultrasonic transducer for generating longitudinal oscillations, the ultrasonic transducer being composed of at least one piezoceramic disc which is arranged within a surrounding casing between a reflector and a horn that carries the metallic probe or sonotrode;
    a guide bush in axial alignment with a hollow of the metallic probe or sonotrode for accommodating an impact member or projectile which is driven in a reciprocating manner, the projectile being arranged for generating an impact force against a mass body on the proximal end of an impact probe, the proximal end projecting backwards into the guide bush;
    said impact probe being passed through an axially extending passage or through-bore of the ultrasonic transducer and through the axially aligned hollow of the sonotrode to thereby place its distal end adjacent to the distal end of the metallic probe or sonotrode.

2. The device according to claim 1, wherein said impact probe is axially adjustable relative to that metallic probe or sonotrode.

3. The device according to claim 1, wherein said axially extending passage or through-bore of the ultrasonic transducer is connected via a transverse bore with a suction duct.

4. The device according to claim 1, wherein said axially extending passage or through-bore of the ultrasonic transducer is sealed by means of a sealing cap which is arranged at the rear side of the reflector.

5. The device according to claim 1, wherein the arrangement comprising said at least one piezoceramic disc, said reflector and said horn of the ultrasonic transducer is fixedly held together by axial tensioning means.

6. The device according to claim 5, wherein an axial protrusion of the reflector being arranged for centering said at least one piezoceramic disc is provided with a threaded portion for its screw connection with the horn to thereby hold together all of the components of the ultrasonic transducer.

7. The device according to claim 1, wherein the ultrasonic transducer is supported on a surrounding casing by elastic supporting means.

8. The device according to claim 1, wherein said guide bush for accommodating said the reversibly driven impact member or projectile is centered in a rear tubular protrusion of the reflector of said ultrasonic transducer.

9. The device according to claim 8, wherein said tubular protrusion of the reflector accommodates a massive and axially bored insert body for seating said guide bush which accommodates said mass body of the impact probe.

10. The device according to claim 9, wherein said insert body comprises a damping element for supporting said mass body on the proximal end of the impact probe.

11. The device according to claim 8, wherein said tubular protrusion of the reflector is seated in a centering bush which itself is centered by the surrounding casing.

12. The device according to claim 11, wherein said centering bush is connected with said insert body via a screw cap which is supported by elastic supporting means on the surrounding casing.

13. The device according to claim 1, wherein said guide bush is provided with an inlet duct for compressed air as a pneumatic drive for the impact member or projectile and is further surrounded by a coaxially arranged outer tube with an annular space inbetween to thereby form a reversing chamber of the pneumatic drive which via a window communicates with a pressure chamber of the guide bush, the reversing chamber being closed by said insert body which is inserted into said outer tube as a closure member which is sealed against said guide bush.

14. The device according to claim 1, wherein all of the structural components of the impact probe are designed as a common subassembly.

15. The device according to claim 14, wherein said common subassembly is adapted for being taken out from the surrounding casing so that only the structural components of the ultrasonic transducer will remain in situ.

* * * * *